United States Patent
Wood

(10) Patent No.: US 8,983,034 B2
(45) Date of Patent: Mar. 17, 2015

(54) X-RAY EXPLOSIVE IMAGER

(75) Inventor: James R. Wood, Grapevine, TX (US)

(73) Assignee: Lockheed Martin Corporation, Grand Prairie, TX (US)

( * ) Notice: Subject to any disclaimer, the term of this patent is extended or adjusted under 35 U.S.C. 154(b) by 377 days.

(21) Appl. No.: 13/368,257

(22) Filed: Feb. 7, 2012

(65) Prior Publication Data

US 2012/0141009 A1 Jun. 7, 2012

Related U.S. Application Data

(63) Continuation of application No. 12/541,539, filed on Aug. 14, 2009, now Pat. No. 8,111,808.

(60) Provisional application No. 61/089,140, filed on Aug. 15, 2008, provisional application No. 61/107,924, filed on Oct. 23, 2008.

(51) Int. Cl.
*G01N 23/203* (2006.01)
*G01V 5/00* (2006.01)
*G01N 24/08* (2006.01)
*G01R 33/44* (2006.01)

(52) U.S. Cl.
CPC .............. *G01V 5/0025* (2013.01); *G01N 23/203* (2013.01); *G01N 2223/053* (2013.01); *G01N 24/084* (2013.01); *G01R 33/441* (2013.01)
USPC ...................... 378/88; 378/57; 378/86; 378/87

(58) Field of Classification Search
CPC .......... G01N 23/203; G01N 2223/052; G01N 2223/053; G01N 2223/323; G01N 2223/345; G01N 2223/425; G01N 2223/60; G01V 5/0008; G01V 5/0016; G01V 5/0025
USPC .............. 378/43, 57, 62, 70, 102, 106, 86–88
See application file for complete search history.

(56) References Cited

U.S. PATENT DOCUMENTS

| | | | |
|---|---|---|---|
| 4,035,616 A | 7/1977 | Piringer | |
| 4,385,549 A | 5/1983 | Bauer et al. | |
| 4,935,616 A | 6/1990 | Scott | |
| 5,044,006 A | 8/1991 | Cyrulnik | |
| 5,206,592 A | 4/1993 | Buess et al. | |
| 5,592,083 A | 1/1997 | Magnuson et al. | |
| 5,608,403 A | 3/1997 | Miller | |

(Continued)

FOREIGN PATENT DOCUMENTS

| JP | 5142396 A | 6/1993 |
|---|---|---|
| WO | 2013082374 A1 | 6/2013 |

OTHER PUBLICATIONS

Carter et al., "A microchannel plate intensified, subnanosecond, x-ray imaging camera," Physica Scripta, vol. 41, pp. 390-395, 1990.

(Continued)

*Primary Examiner* — Thomas R Artman
(74) *Attorney, Agent, or Firm* — Withrow & Terranova, PLLC

(57) ABSTRACT

A technique for use in security screening and detection contexts employs an X-ray explosive imager that acquires images from backscattered RF modulated X-ray signals on which a time series analysis is performed to detect image change across the time series of images that represent pixels changing at the rate of the difference frequency of the RF frequency and the a priori NQR signature frequencies.

20 Claims, 6 Drawing Sheets

(56) References Cited

U.S. PATENT DOCUMENTS

| | | |
|---|---|---|
| 5,635,721 A | 6/1997 | Bardi et al. |
| 5,642,393 A | 6/1997 | Krug et al. |
| 5,696,577 A | 12/1997 | Stettner et al. |
| 5,751,830 A | 5/1998 | Hutchinson |
| 5,754,290 A | 5/1998 | Rajic et al. |
| 5,760,403 A | 6/1998 | Elabd |
| 6,088,423 A | 7/2000 | Krug et al. |
| 6,194,898 B1 | 2/2001 | Magnuson et al. |
| 6,531,225 B1 | 3/2003 | Homme et al. |
| 6,762,420 B2 | 7/2004 | Homme et al. |
| 6,952,163 B2 | 10/2005 | Huey et al. |
| 7,023,956 B2 | 4/2006 | Heaton et al. |
| 7,130,371 B2 | 10/2006 | Elyan et al. |
| 7,135,672 B2 | 11/2006 | Land |
| 7,142,109 B1 | 11/2006 | Frank |
| 7,231,017 B2 | 6/2007 | Gertsenshteyn et al. |
| 7,317,390 B2 | 1/2008 | Huey et al. |
| 7,327,137 B1 | 2/2008 | Crowley et al. |
| 7,344,304 B2 | 3/2008 | Hardesty |
| 7,368,292 B2 | 5/2008 | Hummel et al. |
| 7,385,549 B2 | 6/2008 | Lovberg et al. |
| 7,433,054 B1 | 10/2008 | Tischhauser et al. |
| 7,453,552 B1 | 11/2008 | Miesak |
| 7,646,851 B2 | 1/2010 | Liu et al. |
| 8,111,808 B1 * | 2/2012 | Wood ............... 378/87 |
| 8,411,820 B1 * | 4/2013 | Browder et al. ............... 378/87 |
| 8,411,821 B1 * | 4/2013 | Wood et al. ............... 378/87 |
| 8,433,037 B1 * | 4/2013 | Wood ............... 378/86 |
| 2003/0144800 A1 | 7/2003 | Davis et al. |
| 2004/0165187 A1 | 8/2004 | Koo et al. |
| 2004/0257224 A1 | 12/2004 | Sajkowsky |
| 2005/0079386 A1 | 4/2005 | Brown, Jr. et al. |
| 2005/0099292 A1 | 5/2005 | Sajkowsky |
| 2005/0104603 A1 | 5/2005 | Peschmann et al. |
| 2006/0022140 A1 | 2/2006 | Connelly et al. |
| 2006/0145812 A1 | 7/2006 | Sajkowsky |
| 2007/0008135 A1 | 1/2007 | Sajkowsky |
| 2007/0025512 A1 | 2/2007 | Gertsenshteyn et al. |
| 2007/0211922 A1 | 9/2007 | Crowley et al. |
| 2008/0111545 A1 | 5/2008 | Crowley |
| 2008/0120430 A1 | 5/2008 | Redmond |
| 2014/0133631 A1 * | 5/2014 | Wood ............... 378/88 |

OTHER PUBLICATIONS

Notice of Allowance for U.S. Appl. No. 12/541,539 mailed Sep. 28, 2011, 8 pages.

Non-final Office Action for U.S. Appl. No. 12/541,539 mailed Feb. 10, 2011, 8 pages.

Co-pending U.S. Appl. No. 12/604,548, filed Oct. 23, 2009.

Co-pending U.S. Appl. No. 12/604,626, filed Oct. 23, 2009.

Co-pending U.S. Appl. No. 12/605,002, filed Oct. 23, 2009.

Kozyrev, A.B. et al., "Nonlinear Behavior of Thin Film SrTiO3 Capacitors at Microwave Frequencies," Journal of Applied Physics, vol. 84, Issue 6, Sep. 1998, American Institute of Physics, pp. 3326-3332.

Runkle, Robert C. et al., "Photon and neutron interrogation techniques for chemical explosives detection in air cargo: A critical review," Nuclear Instruments and Methods in Physics Research, Section A: Accelerators, Spectrometers, Detectors and Associated Equipment, vol. 603, Issue 3, May 21, 2009, Elsevier B.V., pp. 510-528.

Yu, Y.H. et al., "Measurement of Thin Film Piezoelectric Constants Using X-ray Diffraction Technique," Physica Scripta, vol. 2007, T129, Dec. 2007, IOP Publishing, pp. 353-357.

International Search Report and Written Opinion for PCT/US2012067217, mailed Mar. 28, 2013, 14 pages.

International Preliminary Report on Patentability and Written Opinion for PCT/US2012/067217, mailed Jun. 12, 2014, 8 pages.

Non-final Rejection for for U.S. Appl. No. 12/604,548, mailed Feb. 22, 2011, 11 pages.

Final Office Action for U.S. Appl. No. 12/604,548, mailed Jun. 3, 2011, 11 pages.

Non-final Rejection for for U.S. Appl. No. 12/604,548, mailed Oct. 25, 2012, 11 pages.

Notice of Allowance for U.S. Appl. No. 12/604,548, mailed Feb. 8, 2013, 5 pages.

* cited by examiner

FIG. 1A
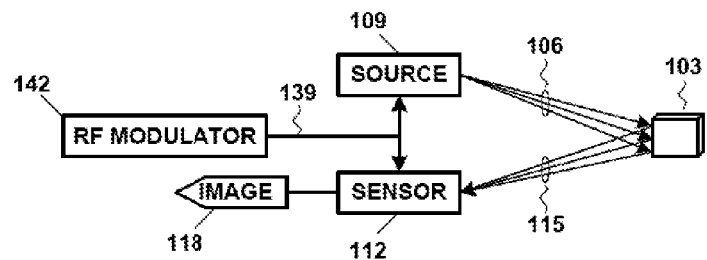
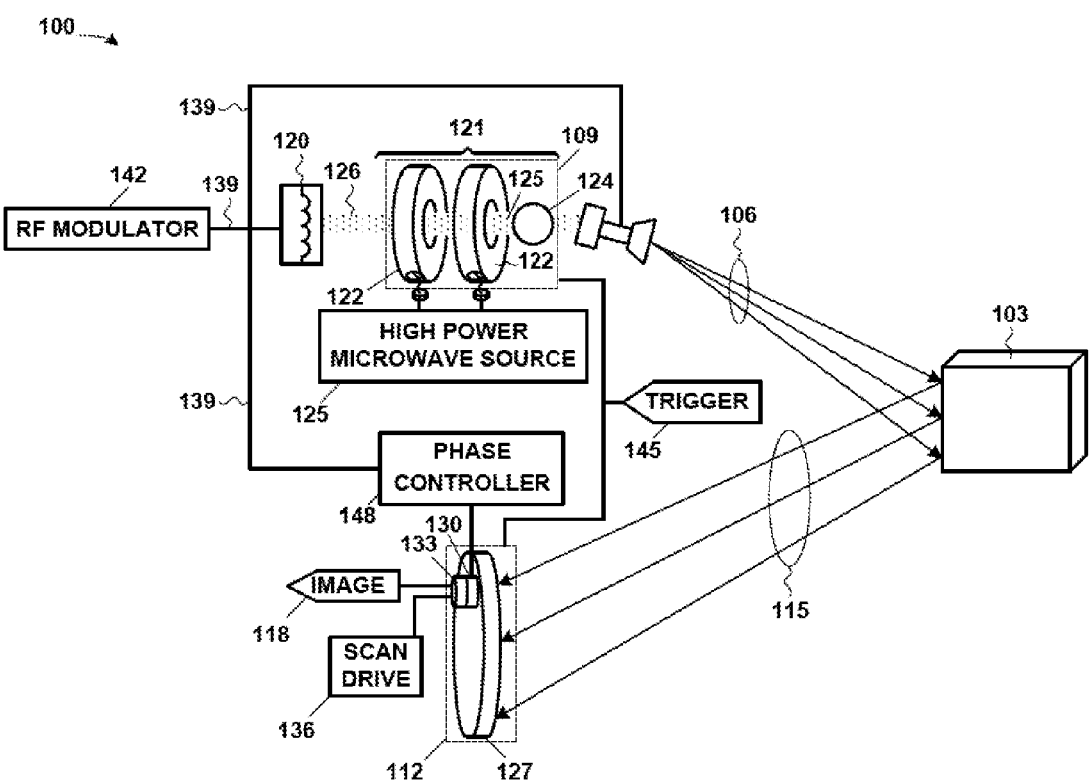
FIG. 1B

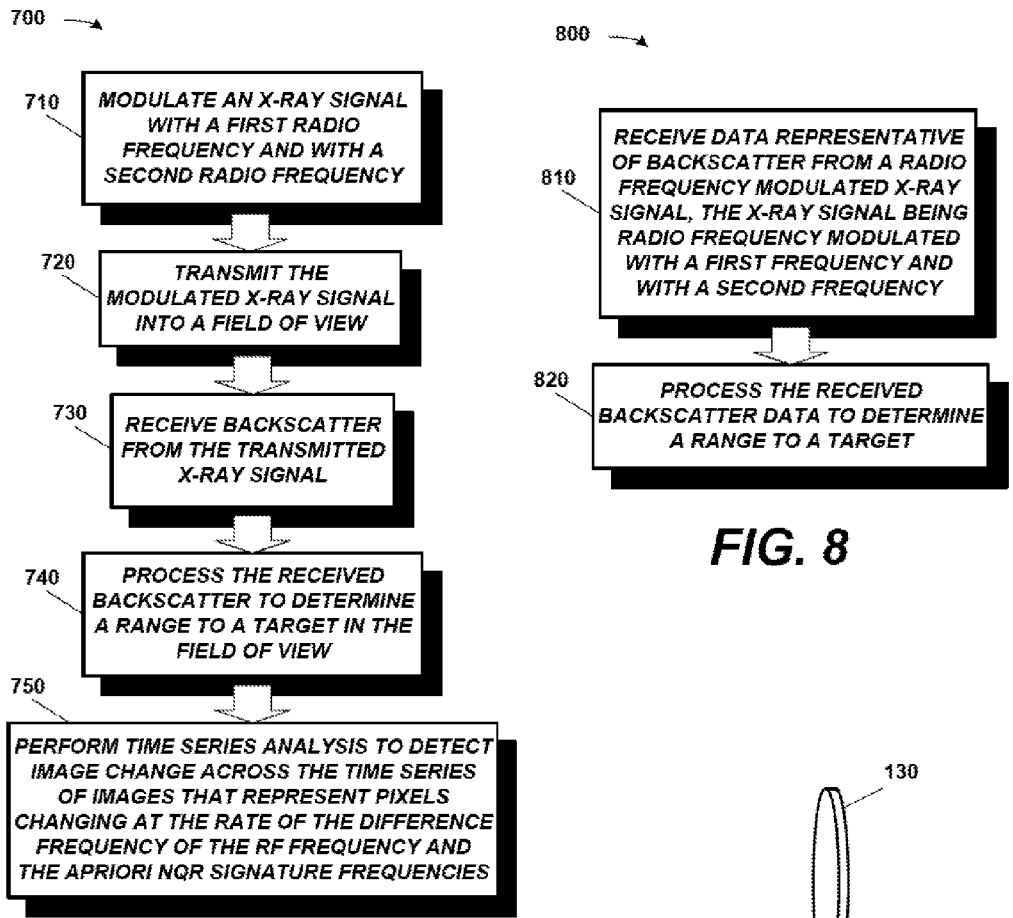
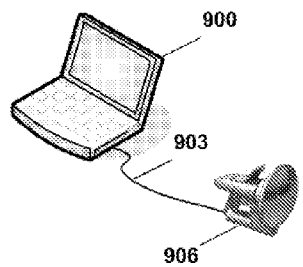
FIG. 9
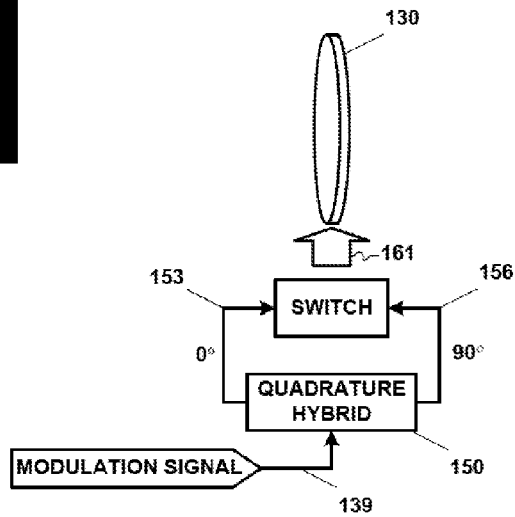
FIG. 1C

X-RAY EXPLOSIVE IMAGER

CROSS REFERENCE TO RELATED APPLICATIONS

This application is a Continuation of copending application Ser. No. 12/541,539 filed on Aug. 14, 2009 now U.S. Pat. No. 8,111,808, which claims priority to Application No. 61/089,140 filed on Aug. 15, 2008. The entire contents of all of the above applications are hereby incorporated by reference. Application Ser. No. 12,541,539 additionally claims priority to Application No. 61/107,924 filed on Oct. 23, 2008.

BACKGROUND OF THE INVENTION

1. Field of the Invention

The present invention pertains to security screening and detection, and, more particularly, to an X-ray explosive imager for use in such endeavors.

2. Description of the Related Art

This section of this document is intended to introduce various aspects of the art that may be related to various aspects of the present invention described and/or claimed below. This section provides background information to facilitate a better understanding of the various aspects of the present invention. As the section's title implies, this is a discussion of related art. That such art is related in no way implies that it is also prior art. The related art may or may not be prior art. It should therefore be understood that the statements in this section of this document are to be read in this light, and not as admissions of prior art.

Conventional three-dimensional ("3D") X-ray images require multiple exposures at multiple angles to image 3D structures. The ability to have portable 3D X-ray systems is limited by the large detector arrays needed for multiple angle imaging, and the size of the imaging volume within the X-ray apparatus.

On a separate note, Nuclear Quadrupole Resonance ("NQR") has been used by detecting the very small radio frequency signals radiated from high energy explosive molecular bonds, when said bonds are excited by an application of electromagnetic energy, usually at radio frequency. However, signals cannot penetrate shielded containers.

The present invention is directed to resolving, or at least reducing, one or all of the problems mentioned above.

SUMMARY OF THE INVENTION

The present invention pertains to security screening and detection, and, more particularly, to an X-ray explosive imager for use in such endeavors. It includes in various aspects, embodiments and implementations, both methods and apparatuses.

In a first aspect, the present invention includes a method, the present invention includes: modulating an X-ray signal with a first radio frequency and with a second radio frequency; transmitting the modulated X-ray signal into a field of view; receiving backscatter from the transmitted X-ray signal; processing the received backscatter to determine a range to a target in the field of view; and performing a time series analysis to detect image change across the time series of images that represent pixels changing at the rate of the difference frequency of the RF frequency and the a priori NQR signature frequencies.

In a second aspect, a software implemented method, the invention includes: receiving data representative of backscatter from a radio frequency modulated X-ray signal, the X-ray signal being radio frequency modulated with a first frequency and with a second frequency; processing the received backscatter data to determine a range to a target; and performing a time series analysis to detect image change across the time series of images that represent pixels changing at the rate of the difference frequency of the RF frequency and the a priori NQR signature frequencies.

In a fourth aspect, a computing apparatus, the invention includes: a processor; a bus system; a storage communicating with the processor over the bus system; and an application residing on the storage. When invoked by the processor, the application performs a software implemented method, comprising: receiving data representative of backscatter from a radio frequency modulated X-ray signal, the X-ray signal being radio frequency modulated with a first frequency and with a second frequency; processing the received backscatter data to determine a range to a target; and performing a time series analysis to detect image change across the time series of images that represent pixels changing at the rate of the difference frequency of the RF frequency and the a priori NQR signature frequencies.

In a fifth aspect, an apparatus, the invention includes: a transmitter and a receiver. The transmitter is capable of: modulating an X-ray signal with a first radio frequency and with a second radio frequency; and transmitting the modulated X-ray signal into a field of view. The receiver is capable of receiving backscatter from the transmitted X-ray signal.

The above presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

BRIEF DESCRIPTION OF THE DRAWINGS

The invention may be understood by reference to the following description taken in conjunction with the accompanying drawings, in which like reference numerals identify like elements, and in which:

FIG. 1A conceptually depicts one particular embodiment of an X-ray microscopy imaging system;

FIG. 1B conceptually illustrates one particular implementation of the X-ray microscopy imaging system of FIG. 1A;

FIG. 1C illustrates a phase controller for the microchannel plate of the X-ray microscopy imaging system implemented as shown in FIG. 1B;

FIG. 7-FIG. 8 illustrate two methods in different aspects of the present invention;

FIG. 9 illustrates still another embodiment; and

Figure 2:
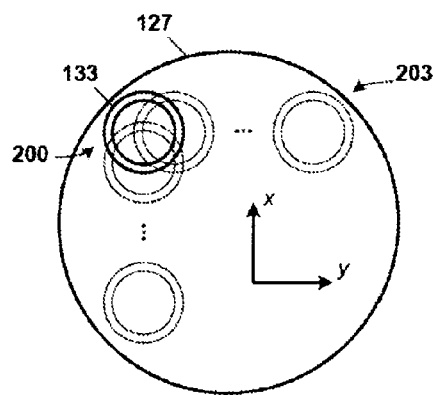
FIG. 2 illustrates the scanning of the detector array across the back of the microchannel plate in the sensor of the embodiment in FIG. 1.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The radio frequency modulation of a high voltage, high energy tube, which can include modulation of amplitude, phase and frequency from a few kilohertz through 5 MHz, is applied across the two faces of a micro channel plate, creating a biasing of the plate that changes with the phase of the applied radio frequency energy. The electron beam energy within the radio frequency tube generates X-rays when electrons strike and decelerate into the beam dump within the tube. The electron beam is amplitude modulated with the radio frequency phase information, and this same amplitude modulation is imparted to the X-rays generated from the electron beam dump. The radio frequency amplitude modulated X-rays propagating from the beam dump within the tube have a preferred conical angle of radiation from the tube volume toward the desired target volume to be examined.

The backscattered X-rays from the target volume will also contain this radio frequency modulation, containing energy modified by the very high energy molecular bonds in explosive materials via nuclear quadrupole resonance of the explosive molecules, and will intercept a scintillation material in front of the phase plate. The scintillation material will fluoresce across an optical frequency range that the micro channel plate is designed to amplify. The resulting amplitude of the micro channel plate light is detected by a detector array and recorded as a digital image.

The resulting amplitude image is a "grayscale" representation of the magnitude of the difference between the radio frequency phase bias on the micro channel plate amplification response and the radio frequency modulated X-ray intensity from the target volume. A subsequent frame of micro channel plate image data with a 90° phase difference between the transmitted X-ray and micro channel plate modulation is recorded. The ratio of the two recorded images creates a resulting image that has a grayscale response proportional to range, rather than X-ray return amplitude.

By taking the arctangent of the ratio of the two images, precise range dependent grayscale increments can be resolved numerically. By creating a series of range images, where pairs of range images have a difference frequency of the amplitude or phase modulation corresponding to a known explosive material nuclear quadrupole resonance line or line pair. A composite of the difference images can create an X-ray image of the explosive volume locations in a given image volume.

Thus, using the technique disclosed herein, X-rays can penetrate and excite nuclear quadrupole resonance ("NQR") in volumes that are shielded from radio frequency excitation. The resultant NQR radio frequency radiation from the molecules can not leave the shielded volume. By looking for the low frequency NQR signals imposed on the radio frequency modulated backscattered X-ray energy, this invention can locate explosives in electromagnetically shielded volumes.

FIG. 1A conceptually illustrates one particular embodiment of an X-ray microscopy imaging system 100. The system 100 is shown subjecting a target volume, or specimen, 103 to a plurality of X-rays 106 (only one indicated) generated and radio-frequency modulated as discussed further below. The system 100 comprises, in general, an X-ray source 109 and a sensor 112.

The X-ray source 109 is capable of emitting the plurality radio-frequency modulated X-rays 106 toward the target volume 103. The sensor 112 is capable of imaging a plurality of X-rays 115 (only one indicated) reflected from the target volume 103 and radio-frequency modulating the image. Radio frequency modulating the image impresses the image with a radio-frequency modulation. Upon imagining the X-rays 115, the sensor 112 then outputs the radio-frequency modulated image 118. The structure and operation of the X-ray source 109 and sensor 112 in the illustrated embodiment will now be discussed in further detail.

Referring now to FIG. 1B, X-ray source 109 of the illustrated embodiment includes a filament 120, a radio-frequency modulated tube 121, and a high power microwave source 125. The filament 120 generates an electron beam 126 output to the radio frequency modulated tube 121. The radio frequency modulated tube comprises a pair of cavity resonator structures 122 and a high power (e.g., 2 Joules/pulse) microwave source 127 that give rise to the magnetic or electric fields that deflect the electron beam 125 and impart the intensity modulation of the electron beam 125 at radio frequency and an electron beam dump 124. The rotator 131 then imparts the radio frequency modulated x-rays 106 toward the target 103.

The radio-frequency modulated tube 121 is a high voltage, high energy tube. The radio-frequency modulated tube 121 may be, for example, a Klystron, such as is known in the art. Suitable implementations for the X-ray source 109 are commercially available off the shelf. For example, the NIR MCP-PMT and X-Ray Scintillator line of products offered by Hamamatsu Corp. offer several suitable alternatives. Hamamatsu Corp. can be reached in the United States at: 360 Foothill Rd, Bridgewater, N.J. 08807, ph: 908-231-0960; fax: 908-231-1218. Additional information can be obtained through those contacts or at www.hamamatsu.com over the World Wide Web of the Internet.

The sensor 112 of the illustrated embodiment comprises three parts. It includes a layer of a scintillating material 127 capable of intercepting the X-rays 115 emanating from the target volume 103 and fluorescing light (not shown) correlated thereto. A radio-frequency modulated microchannel plate 130 is located behind the scintillating material 127 to detect and amplify the fluoresced light. The microchannel plate 130 may also be referred to as a "phase plate". The amplification of the fluoresced light may also be described as "intensifying" the image, and so the microchannel plate 130 may be considered an "image intensifier". A detector array 133 is placed to detect the amplified fluorescent light output by the radio-frequency modulated microchannel plate 130. Again, suitable implementations are commercially available off the shelf, including the X-Ray Scintillator line of products offered by Hamamatsu Corp. mentioned above. Furthermore, information regarding imaging with such sensors and their fabrication is available from U.S. Pat. Nos. 6,531,225 and 6,762,420.

In the particular embodiment illustrated in FIG. 1B, the detector array 133 is not large enough to cover the entire back of the microchannel plate 130 simultaneously. The illustrated embodiment therefore includes a scan drive 136 that scans the detector array 133 from one position 200, shown in FIG. 2 in solid lines, to other positions 203 (only one indicated), shown in broken lines, across the back 131 of the microchannel plate 136. Such scan drives are known to the art and the scan drive 136 can be implemented using any suitable scan drive known to the art.

The illustrated embodiment also employs what is known as "range gating". In range gating, the output of the detector array 133 is used only during certain time periods when X-rays 115 of interest are expected to be received. These time periods typically are determined from trigger times and expected "time of flight" for the X-rays 115. Thus, the sensor 112 will need to know when the X-rays 115 are triggered. This can be accomplished by feeding the trigger signal 145 to the radio-frequency modulated tube 121 to the sensor 112 as well. The gating itself can be implemented by controlling power to the sensor 112 so that it is operational only at the desired times or by discarding the output of the sensor 112 during the "off" periods. Alternative embodiments may employ other gating techniques that may become apparent to those skilled in the art having the benefit of this disclosure.

The X-ray source 109 receives a modulation signal 139 from a radio-frequency ("RF") modulator 142. The modulation signal 139 is also input to the sensor 112. The radio frequency modulation of the directed energy tube 112, which can include modulation of amplitude, phase and/or frequency from a few kilohertz (e.g., 3 KHz) through 300 GHz, is applied across the two faces of the microchannel plate 130. Those in the art will recognize that, practically, the state of art in x-ray fluorescent imaging materials is at ~10 GHz, but "direct detection" of x-ray energy by new solid state detectors may very well have growth to 300 GHz. Typically, modulation will hold on one center frequency and amplitude/phase modulate, although some embodiments may modulate all three at once. This creates a biasing of the microchannel plate 130 that changes the recorded intensity of the image 118 as a function of range dependent phases of the transmitted radio frequency modulated X-ray energy.

In operation, the electron beam energy 145 within the radio frequency, radio-frequency modulated tube 121 generates the X-rays 106 when electrons (not shown) strike and decelerate into the beam dump 124 within the tube 121. The electron beam energy 145 is amplitude modulated, in this particular embodiment, with the radio frequency phase information of the modulation signal 139. This same amplitude modulation is imparted to the X-rays 106 generated from the electron beam dump 124.

The radio frequency amplitude modulated X-rays 106 propagating from the electron beam dump 124 within the radio-frequency modulated tube 121 have a preferred conical angle α, conceptually illustrated in FIG. 1B, of radiation from the tube volume toward the desired target volume 103 to be examined. The expanding cone a of X-rays 106 from the virtual point source of the electron beam dump 124 within the radio-frequency modulated tube 121 provides a means of casting a magnified shadow of an object placed in the path between the X-ray source 109 and a scintillator material 127. The reflected X-rays 115 through the target volume will also contain this radio frequency modulation, containing energy modified by the materials in the object to be X-ray imaged.

The reflected X-rays 115 intercept the scintillation material 127 in front of the radio frequency modulated microchannel plate 130. The scintillation material 127 fluoresces across an optical frequency range that the microchannel plate 130 is designed to amplify. The scintillation material 127 has a time constant small enough that the amplitude of the fluorescence follows the radio frequency modulation rate. The resulting modulated microchannel plate light (not shown) is detected by the detector array 133 and recorded as the digital image 118.

The resulting amplitude image 118 is a set of ordered data that is a "grayscale" representation of the magnitude of the difference between the radio frequency phase bias on the microchannel plate 130 amplification response and the radio frequency modulated X-ray 106 intensity through the target volume 103. In practice, as series of images 118 are captured over time, each representing a sampling of the reflected X-rays 115. The image 118 may be stored, rendered for human perception, processed for some further use, or any combination thereof.

For a given image 118, a subsequent frame of microchannel plate image data with a 90° phase difference between the transmitted X-ray and microchannel plate modulation is recorded. That is, between two successive images 118, there is a 90° phase difference between those quantities. This is implemented by the phase controller 148, first shown in FIG. 1B and better illustrated in FIG. 1C. As shown in FIG. 1C, a quadrature hybrid 150 receives the modulation signal 139 from the RF modulator 142, shown in FIG. 1B. The quadrature hybrid 150 then, responsive to the modulation signal 139, outputs either a 0° phase offset control signal 153 or a 90° phase offset control signal 156 to a switch 159. The switch 159 then, in response to the phase offset control signals 153, 156, outputs a phase control signal 161 to control phase offset of the microchannel plate 130.

The ratio of the two recorded images 118 creates a resulting image (not shown) that has a grayscale response proportional to range, rather than X-ray return amplitude. By taking the arctangent of the ratio of the two images 118, precise range-dependent grayscale increments can be resolved numerically. Note also that, by taking successive images 118, the target can be imaged in three dimensions.

Figure 3:
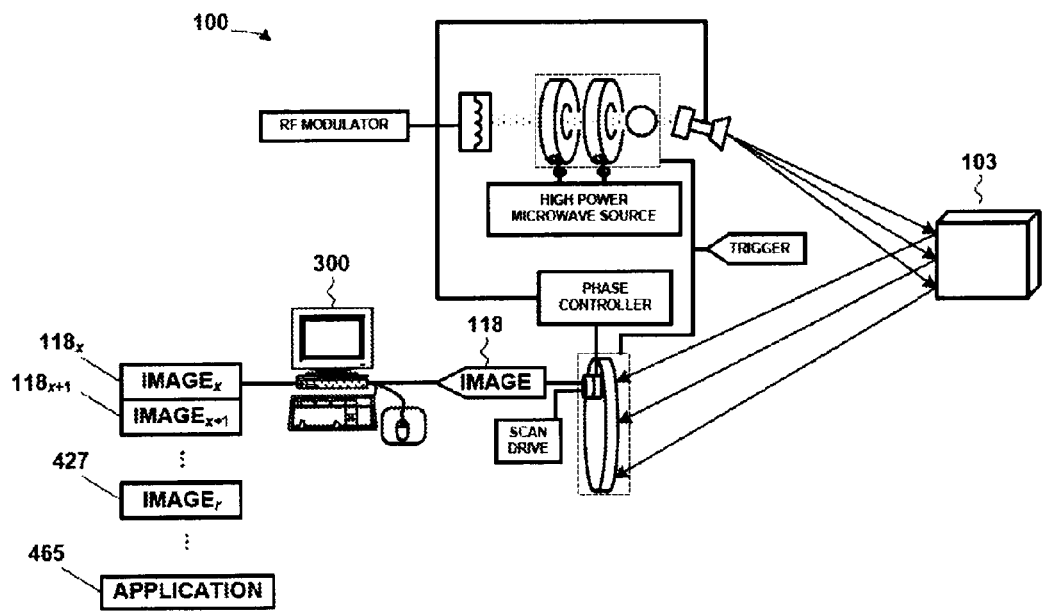
FIG. 3 depicts a second embodiment wherein the X-ray microscopy imaging system of FIG. 1B is deployed with a computing apparatus for image processing.

To that end, the X-ray microscopy imaging system 100 shown in FIG. 1B will typically be deployed in association with a computing apparatus 300, shown in FIG. 3. The computing apparatus 300 in the illustrated embodiment is a stand-alone work station. In alternative embodiments, the computing apparatus may be embedded in the apparatus 100 or may be part of a larger computing system. Instead of a workstation, the computing apparatus could be implemented in a desktop, laptop, notebook, etc., in other embodiments. The present invention admits wide variation in the implementation of the computing apparatus 300.

Figure 4:
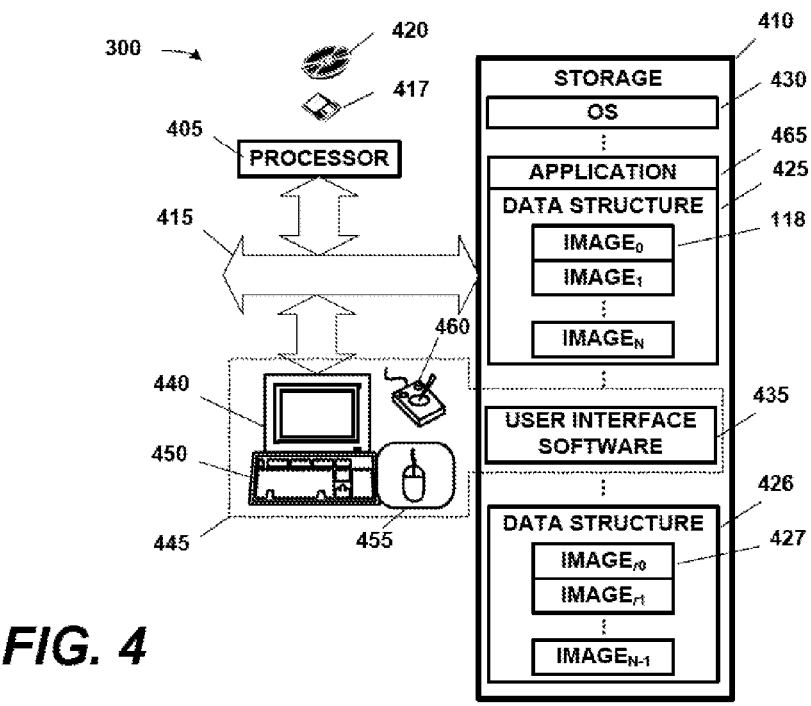
FIG. 4 shows selected portions of the hardware and software architecture of a computing apparatus such as may be employed in some aspects of the embodiments disclosed herein.

In one aspect, the present invention is a software implemented method for generating an X-ray image that has a grayscale response proportional to range. FIG. 4 shows selected portions of the hardware and software architecture of the computing apparatus 300, first shown in FIG. 3, such as may be employed in some aspects of the present invention.

The computing apparatus 300 includes a processor 405 communicating with storage 410 over a bus system 415.

The present invention admits wide variation in the implementation of the processor 405. Certain types of processors may be more desirable than others for some embodiments. For instance, a digital signal processor ("DSP") or graphics processor may be more desirable for the illustrated embodiment than will be a general purpose microprocessor. Other video handling capabilities might also be desirable. For instance, a Joint Photographic Experts Group ("JPEG") or other video compression capability and/or multi-media extension may be desirable. In some embodiments, the processor 405 may be implemented as a processor set, such as a microprocessor with a graphics co-processor, particularly for server architectures.

The storage 410 may be implemented in conventional fashion and may include a variety of types of storage, such as a hard disk and/or random access memory ("RAM") and/or removable storage such as a magnetic disk (not shown) or an optical disk (also not shown). The storage 410 will typically involve both read-only and writable memory. The storage 410 will typically be implemented in magnetic media (e.g., magnetic tape or magnetic disk), although other types of media may be employed in some embodiments (e.g., optical disk). The storage 410 may also employ various virtual memory and other memory management techniques. The present invention admits wide latitude in implementation of the storage 410 in various embodiments. In the illustrated embodiment, the storage 410 is internal memory implemented in a hard disk main memory, RAM, and in cache.

The bus system 415 will also vary widely by implementation. Depending upon the implementation, the bus system 415 may comprise an internal bus, a network backbone, or some combination thereof. For example, if the computing apparatus 300 is instead embedded with the X-ray microscopy imaging system 100, the bus system 415 may be implemented as an internal bus. On the other hand, if the computing apparatus 300 is but a part of a larger computing system across which the computing functionalities are distributed, then some type of external bus—i.e., a network backbone—will be employed. Either way, the bus system 415 may be implemented using conventional technologies.

The storage 410 is also encoded with an operating system ("OS") 430, user interface software 435, and an application 465. The user interface software 435, in conjunction with a display 440, implements a user interface 445. The user interface 445 may include peripheral input/output devices such as a keypad or keyboard 450, a mouse 455, or a joystick 460. The processor 405 runs under the control of the operating system 430, which may be practically any operating system known to the art. The application 465 may be invoked by the operating system 430 upon power up, reset, or both, depending on the implementation of the operating system 430. The application 465, when invoked, performs the method of the present invention. The user may also invoke the application 465 in conventional fashion through the user interface 445.

The storage 410 is also encoded with two data structures 425, 426. The data structure 425 contains the images 118 (only one indicated) that are acquired as described above. The data structure 426 contains the resultant images 427 (only one indicated) generated by the application 465 through the process generally described above. Thus, each resultant image 427 is an X-ray image that has a grayscale response proportional to range. The data structures 425, 426 may be implemented in any suitable type of data structure known to the art, such as a database, a list, or a queue. The data structures 425, 426 may be designed for long term storage of the images 118, 427 or to temporarily buffer them, depending on the implementation.

As mentioned above, the hardware and software architecture shown in FIG. 4 is exemplary only, and may find wide variation across numerous alternative embodiments. A good example of such variation is the implementation of the data structures 425, 426 described immediately above. Another good example is in the application 465. In other embodiments, the functionality residing in the application 465 may instead repose in some other kind of software component, such as a script, a daemon, etc.

There similarly may be variation in the situs of the various elements of the software aspects of the architecture. For example, there is no need for the images 118, 427 to reside on the same computing apparatus 300 or to reside on the same computing apparatus 300 as the application 465 by which they are processed and created. Some embodiments of the present invention may be implemented on a computing system, e.g., the computing system 500 in FIG. 5, comprising more than one computing apparatus. The computing system 500 employs a networked client/server architecture, but other architectures may be used.

Figure 5:
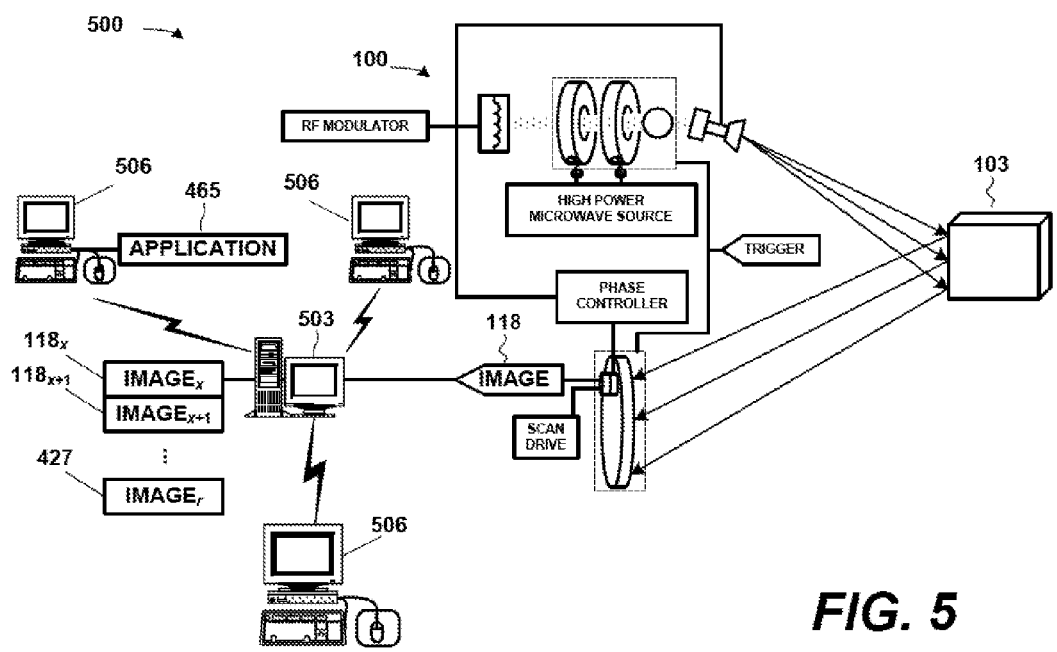
FIG. 5 illustrates a computing system on which some aspects of the illustrated embodiments may be practiced in some implementations.

In the embodiment of FIG. 5, the images 118, 427 (only one of each indicated) all reside in a data structure (not shown) residing on a server 503. The application 465 by which they are processed, however, resides on a workstation 506. Furthermore, although the images 118, 427 are all shown residing on the server 503, there is no requirement that they reside together. The images 118 might reside on the server 503 while the resultant images 427 might reside on the workstation 506. The invention admits wide variation in this respect.

Note that there is no requirement that the computing system 500 be networked. Alternative embodiments may employ, for instance, a peer-to-peer architecture or some hybrid of a peer-to-peer and client/server architecture. The size and geographic scope of the computing system 500 is not material to the practice of the invention. The size and scope may range anywhere from just a few machines of a Local Area Network ("LAN") located in the same room to many hundreds or thousands of machines globally distributed in an enterprise computing system.

Figure 6B:
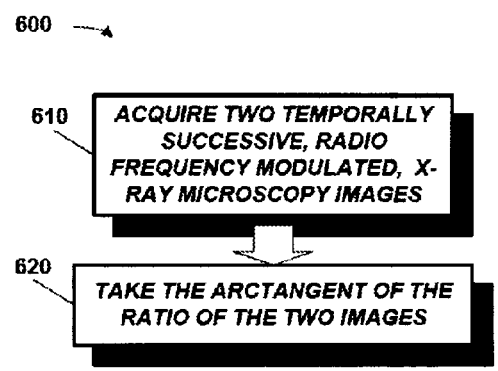
FIG. 6B is a flowchart of one particular embodiment of a method for acquiring and processing X-ray microscopy images.
Figure 6A:
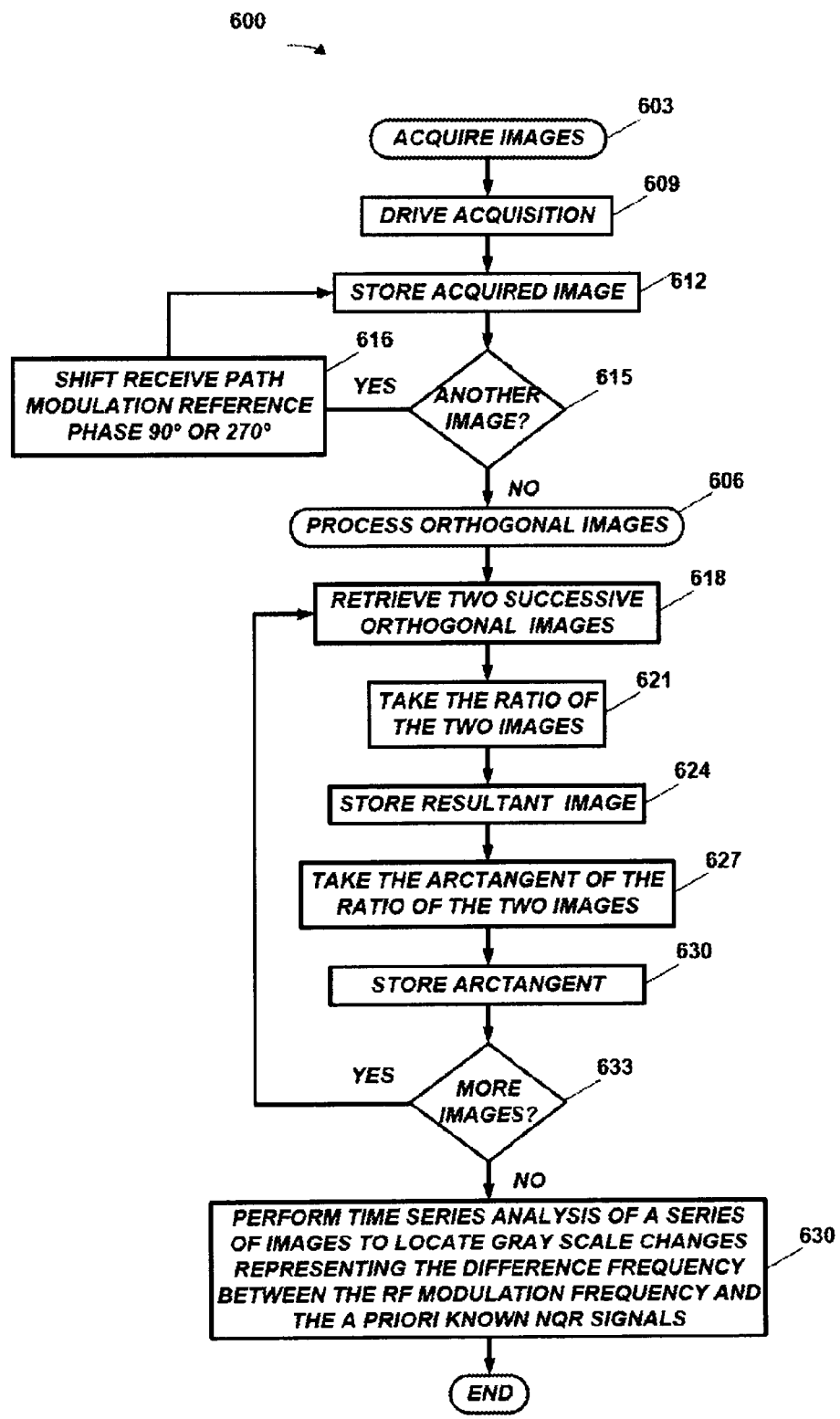
FIG. 6A is a computer-implemented method for generating an X-ray image that has a grayscale response proportional to range.

Turning now to both FIG. 3 and FIG. 6A, in operation, the application 465 of the illustrated embodiment executes the process 600. The process 600 is performed in two parts—image acquisition (at 603) and image processing (at 606). In this particular embodiment, all acquisition occurs prior to processing. Alternative embodiments may "process on the fly", or process the images 118, shown in FIG. 1B, as they are acquired. The difference will create some differences in handling having both advantages and disadvantages relative to the illustrated embodiment. Those in the art having the benefit of this disclosure will appreciate not only these relative advantages and disadvantages, but also the differences in handling and will be able to implement such alternatives should they wish to do so.

The application 465 first drives (at 609) the acquisition of the images 118. Successive images will be orthogonal in the sense that they are taken with 90° shifts in receive path modulation between two successive images 118. That is, one image will be RF biased without a phase offset and the next will be RF biased with a 90° phase offset by virtue of the RF modulation of the sensor 112 as described above. This includes generating and transmitting the control signals for the X-ray trigger, the RF modulation, and the scanning and detection as described above.

Figure 10:
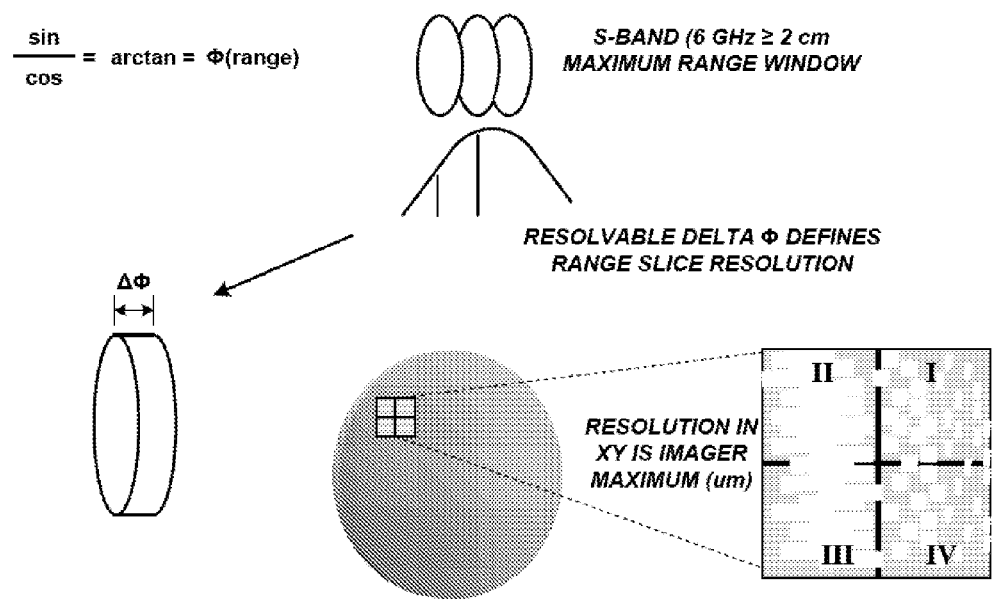
FIG. 10 graphically represents the range slicing practice in the illustrated embodiments.

The successive images 118 represent "range slicing" through range gating as a function of amplitude. This is graphically presented in FIG. 10 for one particular embodiment. The resolvable difference, which will be implementation specific, between successive images 118 will determine the range slice resolution.

The images 118 are captured over time and stored (at 612). This continues until all the images 118 are captured and stored (at 615). Note that, after capturing any given image 118, the receive path modulation reference phase is shifted (at 616) 90° or 270° before storing (at 612) the next image 118.

Once acquisition (at 603) is finished, processing (at 606) begins. The application 465 processes the images 118 by first retrieving (at 618) two successive images 118. "Successive" in this instance means they follow one another in time at acquisition. As noted above, those two images 118 will exhibit a 90° phase difference between the transmitted X-ray and microchannel plate modulation. Consequently, the ratio of the two images 118 creates a resulting image 427 that has a grayscale response proportional to range, rather than X-ray return amplitude.

The application 465 takes the ratio (at 621) and stores (at 624) the resultant image 427. The application 465 then takes (at 627) the arctangent of the ratio of the two images 118 to numerically resolve precise range-dependent grayscale increments of the resultant image 427 and stores (at 630) them. The application does this for each of pair of images 118 (at 633) until there are no more pairs of images 118. The process continues (at 633), in this embodiment, until all images 118 are acquired. Once the images are acquired, a time series analysis is preformed on a series of images to locate gray scale changes representing the difference frequency between the RF modulation frequency and the a priori known NQR signals Thus, in one aspect, the invention includes a method 600, shown in FIG. 6B. The method 600 is a computer-implemented method for generating an X-ray image that has a grayscale response proportional to range. The method 600 comprises (1) acquiring two temporally successive, radio frequency modulated, X-ray images (at 610); and (2) taking the arctangent of the ratio of the two images (at 620).

Note, however, that the method 600 is but one particular embodiment by which the method of the invention may be practiced. For example, in alternative embodiments, an image can be taken without transmit or receive modulation, prior to or successive to the phase modulated images, to improve extraction of the phase information. Still other alternative embodiments may use two successive orthogonal phase modulated images, to be added together, or processed as "square root of the sum of the squares" of the intensities of the successive orthogonal phase images to establish a reference image level to improve extraction of phase information from intensity artifacts in the image. This can be done in place of the unmodulated image step in process just described immediately above in this paragraph, or in addition to the unmodulated image.

As is apparent from the discussion above, some portions of the detailed descriptions herein are consequently presented in terms of a software implemented process involving symbolic representations of operations on data bits within a memory in a computing system or a computing device. These descriptions and representations are the means used by those in the art to most effectively convey the substance of their work to others skilled in the art. The process and operation require physical manipulations of physical quantities. Usually, though not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated or otherwise as may be apparent, throughout the present disclosure, these descriptions refer to the action and processes of an electronic device, that manipulates and transforms data represented as physical (electronic, magnetic, or optical) quantities within some electronic device's storage into other data similarly represented as physical quantities within the storage, or in transmission or display devices. Exemplary of the terms denoting such a description are, without limitation, the terms "processing," "computing," "calculating," "determining," "displaying," and the like.

Note also that the software implemented aspects of the invention are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The invention is not limited by these aspects of any given implementation.

Furthermore, portions of this disclosure include discussion of "images". These images are shown in a human-perceptible form, i.e., in a hard copy. Note that this presentation is for the sake of illustration. The images are actually collections or sets of ordered data. In the illustrated embodiments, the data is three-dimensional. The images may be rendered to make them perceptible by image analysts in some embodiments. For example, the images may be rendered for output in hard copy, or they may be rendered and displayed electronically. However, some embodiments of the invention may be practiced automatically, that is, without human interaction. Thus, some embodiments may be practiced without the images being so rendered.

The combination of the x-ray energy frequency and the range slicing described above produces improved image contrast. This improved image contrast can provide image from which items within a container of some sort can more readily be identified relative to conventional approaches. However, the present invention combines the improved image contrast with Nuclear Quadrupole Resonance ("NQR") detection, as well.

Once the images have been acquired and processed as described above, the explosives can be detected therefrom using NQR. As an example, most explosives contain $^{14}N$, which has a large quadrupole moment. The NQR frequency is determined by interaction with electric field gradient in a crystal. Each material has a very specific resonance frequency with a linewidth of ~1 kHz. A time series analysis can be performed on the range slice data acquired as described above to extract the NQR signature of the materials therein. The NQR signature being specific to the material, the material can be identified.

Suitable techniques for detecting NQR signatures are known. One suitable technique that may be modified for use with the present invention is disclosed in U.S. Pat. No. 5,206,592, entitled "Detection of Explosives by Nuclear Quadrupole Resonance", issued Apr. 27, 1993 to the inventors Michael L. Buess, et al. To further an understanding of the present invention, a portion of this patent will now be excerpted with some modification for implementation in the present invention.

The technique includes a system for detecting a class of explosives and narcotics containing nitrogen in a specimen by nuclear quadrupole resonance. As discussed above, the apparatus comprises pulse generating means for generating a train of radio frequency pulses having a predetermined frequency, an RF modulated X-ray signal for irradiating the specimen with the train of radio frequency pulses and detecting an integrated nitrogen signal in response to irradiating the specimen, coupling means for transmitting the train of radio frequency pulses to the X-Ray signal source and receiving the nitrogen signal from a time series of image samples, with the images taken at RF modulation frequencies near the NQR resonance frequency of interest, with the RF modulation frequency offset from the RF frequency such that the difference frequency of the NQR resonance and the RF frequency captures in the time series of image samples as a change in pixel intensity at the location of explosive or narcotic in the image, such that the time series of greyscale images provides the difference frequency of the a priori known NQR resonance and RF X-ray modulation frequencies. Because the NQR resonance frequency of a quadrupolar nucleus in a crystalline solid is well-defined and is especially sensitive to the chemical structure, false alarms from nitrogenous materials having NQR resonances at frequencies other than the characteristic frequencies of the explosives are not a problem.

While the technique disclosed herein will produce a very low rate of false alarms, it also will generally suffer form a low signal to noise ratio. However, under even very good condition, the signal to noise ratio will be ~0.5 with conventional RF detection. Accordingly, this is not a strong negative relative to conventional techniques.

Thus, in one aspect, the present invention provides a method, such as the method 700 illustrated in FIG. 7. The method 700 comprises modulating (at 710) an X-ray signal with a first radio frequency and with a second radio frequency. The modulated X-ray signal is then transmitted (at 720) into a field of view. Backscatter from the transmitted X-ray signal is received (at 730) and processed (at 740) to determine a range to a target in the field of view. Then, a time series analysis is performed (at 745) to detect image change across the time series of images that represent pixels changing at the rate of the difference frequency of the RF frequency and the apriori NQR signature frequencies As noted above, some aspects of the method are software implemented. Thus, in one aspect, a software component (e.g., the application 465, in FIG. 4) performs a method such as the method 800. The method 800 comprises receiving (at 810) data representative of backscatter from a radio frequency modulated X-ray signal, the X-ray signal being radio frequency modulated with a first frequency and with a second frequency. The received backscatter data is then processed (at 820) to determine a range to a target.

The invention admits some latitude in the implementation of both the apparatus and method of the invention. For example, a suitable handled X-ray device suitable for modification to implement the presently disclosed technique is the LEXID™ X-ray Imaging Device available from Physical Optics Corporation, at 0600 Gramercy Place, Torrance, Calif. 90501-1821, Phone: 310-320-3088, Fax: 310-320-5961. In particular, the device would be modified to implement the modulation technique disclosed herein. Additional information is available over the World Wide Web of the Internet at their website <http://www.poc.com/default.asp>. Principles of operation, construction, and design are also disclosed in U.S. Pat. No. 7,231,017.

Using such a handheld device, however, the computing apparatus of FIG. 4 will more typically be embodied in a laptop 900, shown in FIG. 9, receiving the received backscatter from a sensor through a peripheral connection 903 from a handheld sensor 906. The processing may even be performed in the handheld sensor 906 itself in some embodiments.

The apparatus of the presently disclosed technique and its constituent parts are "capable of" their various functionalities in the sense that they perform their function when properly powered and controlled but do not do so in the absence of power and control. Thus, in operation, the apparatus is "capable of" performing the associated methods disclosed herein. The apparatus is otherwise "capable of" performing the associated methods.

Thus, in one aspect, the presently disclosed technique combines existing range gating methods used in optical radar or light detection and ranging ("LIDAR") with a novel method of x-ray generation using high energy radio frequency sources. The invention allows portable 3D imaging with reduction in radiation exposure, and improved image quality due to range gating reduction of interfering X-ray energy.

The following documents are hereby incorporated by reference as if set forth verbatim herein for the reasons set forth:

U.S. Provisional Application Ser. No. 61/089,140, entitled "X-Ray Explosive Imager", and filed Aug. 15, 2008, in the name of the inventor J. Richard Wood, for all teachings and all purposes;

Japanese patent document JP 5-142396 for its teachings regarding X-ray telescopes;

U.S. Pat. No. 4,035,616, entitled, "Range Imaging Laser RADAR", issued Jun. 19, 1990, to The United States of America as assignee of the inventor Marion W. Scott, for its teachings regarding RF amplitude modulation using MCPs and range gating the receipt of backscatter;

U.S. Pat. No. 4,935,616, entitled "Range imaging laser radar", and issued Jun. 19, 1990, to The United States of America as represented by the Department of Energy as assignee of the inventor Marion W. Scott.

M. R. Carter, et al., "A Microchannel Plate Intensified, Subnanosecond, X-ray Imaging Camera", 41 *Physica Scripta* 390-395 (1990), for its teachings regarding the design, construction, and operation of MCP assemblies; and U.S. Pat. No. 7,231,017, entitled "Lobster Eye X-ray Imaging System and Method of Fabrications Thereof", issued Jun. 12, 2007, to Physical Optics Corporation as assignee of the inventors Michael Gertsenshteyn, et al., in its entirety and for all of its teachings;

U.S. Application Ser. No. 11/191,095, entitled "Lobster Eye X-ray Imaging System and Method of Fabrications Thereof", filed Jul. 27, 2005, in the name of the inventors Michael Gertsenshteyn, et al., and assigned to Physical Optics Corporation, and published as U.S. Patent Publication 2007/0025512 on Feb. 1, 2007, in its entirety and for all of its teachings;

U.S. Pat. No. 5,206,592, entitled "Detection of Explosives by Nuclear Quadrupole Resonance", issued Apr. 27, 1993 to the inventors Michael L. Buess, et al.; and U.S. Pat. No. 5,696,577, entitled "3D Imaging Underwater Laser Radar", issued Dec. 9, 1997, to Advanced Scientific Concepts, Inc. in the name of the inventors Roger Stettner and Howeard W. Bailey, for its teachings regarding range slicing.

Each of these documents is also hereby incorporated by reference for the respective teachings noted above as if set forth herein verbatim.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
    modulating an X-ray signal with a first radio frequency and with a second radio frequency to generate a modulated X-ray signal;
    transmitting the modulated X-ray signal toward a container that contains an item;
    detecting modulated X-ray signal backscatter from the item; and
    processing the modulated X-ray signal backscatter to identify a chemical element in the item based on differences in the modulated X-ray signal backscatter over time that occur at a rate associated with a nuclear quadrupole resonance of the chemical element.

2. The method of claim 1, wherein the container is electromagnetically shielded.

3. The method of claim 1, wherein the chemical element is associated with an explosive material.

4. The method of claim 1, wherein processing the modulated X-ray signal backscatter to identify the chemical element further comprises:
    iteratively detecting, over a period of time, the modulated X-ray signal backscatter to generate a plurality images;
    determining a frequency of change in the plurality of images with respect to the modulated X-ray signal; and
    based on the frequency of change, identifying the chemical element.

5. The method of claim 4, wherein iteratively detecting the modulated X-ray signal backscatter further comprises:
    receiving, by a scintillation material, the modulated X-ray signal backscatter;
    generating, by the scintillation material, fluoresced light in response to receiving the modulated X-ray signal backscatter;
    amplifying, by a micro-channel plate, the fluoresced light to generate amplified fluoresced light; and
    detecting, by a detector array, the fluoresced light.

6. The method of claim 1, further comprising:
    determining a range to the chemical element in the item by taking an arctangent of a ratio of two successive images of the modulated X-ray signal backscatter.

7. The method of claim 1, further comprising range-gating receipt of the modulated X-ray signal backscatter.

8. The method of claim 1, further comprising processing the modulated X-ray signal backscatter to generate a three-dimensional image depicting the item, a location of the chemical element in the item.

9. The method of claim 8, further comprising rendering the three-dimensional image.

10. The method of claim 1, wherein processing the modulated X-ray signal backscatter to identify the chemical element in the item based on the differences in the modulated X-ray signal backscatter over time that occur at the rate associated with the nuclear quadrupole resonance of the chemical element further comprises:
    generating, based on the processing of the modulated X-ray signal backscatter a nuclear quadrupole resonance (NQR) signature;
    comparing the NQR signature to a plurality of predetermined NQR signatures; and
    determining that the NQR signature matches a predetermined NQR signature of the chemical element.

11. A method, comprising:
    receiving, by a sensor, modulated X-ray signal backscatter representative of backscatter from a radio frequency modulated X-ray signal, the radio frequency modulated X-ray signal being radio frequency modulated with a first frequency and with a second frequency; and
    processing, by a computing device communicatively coupled to the sensor, the modulated X-ray signal backscatter to identify a chemical element in an item based on differences in the modulated X-ray signal backscatter over time that occur at a rate associated with a nuclear quadrupole resonance of the chemical element.

12. The method of claim 11, wherein processing the modulated X-ray signal backscatter includes:
    determining ratios between data representing the modulated X-ray signal backscatter modulated at the first frequency and data representing the modulated X-ray signal backscatter modulated by the second frequency; and
    numerically resolving the ratios into range dependent increments.

13. The method of claim 11, wherein numerically resolving the ratios includes taking an arctangent of the ratios.

14. The method of claim 11, further comprising rendering the modulated X-ray signal backscatter.

15. A non-transitory program storage medium encoded with instructions that, when executed by a computing device, performs a method comprising:
    receiving modulated X-ray signal backscatter representative of backscatter from a radio frequency modulated X-ray signal, the radio frequency modulated X-ray signal being radio frequency modulated with a first frequency and with a second frequency; and
    processing the modulated X-ray signal backscatter to identify a chemical element in an item based on differences in the modulated X-ray signal backscatter over time that occur at a rate associated with a nuclear quadrupole resonance of the chemical element.

16. The non-transitory program storage medium of claim 15, wherein processing the modulated X-ray signal backscatter includes:
    determining ratios between data representing the modulated X-ray signal backscatter modulated at the first frequency and data representing the modulated X-ray signal backscatter modulated by the second frequency; and
    numerically resolving the ratios into range dependent increments.

17. The non-transitory program storage medium of claim 16, wherein numerically resolving the ratios includes taking an arctangent of the ratios.

18. The non-transitory program storage medium of claim 16, further comprising rendering the modulated X-ray signal backscatter.

19. A computing apparatus, comprising:
    a processor;
    a bus system;

a storage communicating with the processor over the bus system; and an application residing on the storage that, when invoked by the processor, is configured to:

receive modulated X-ray signal backscatter representative of backscatter from a radio frequency modulated X-ray signal, the radio frequency modulated X-ray signal being radio frequency modulated with a first frequency and with a second frequency; and process the modulated X-ray signal backscatter to identify a chemical element in an item based on differences in the modulated X-ray signal backscatter over time that occur at a rate associated with a nuclear quadrupole resonance of the chemical element.

20. The computing apparatus of claim 19, wherein the computing apparatus is portable.

* * * * *

UNITED STATES PATENT AND TRADEMARK OFFICE
CERTIFICATE OF CORRECTION

| | | |
|---|---|---|
| PATENT NO. | : 8,983,034 B2 | |
| APPLICATION NO. | : 13/368257 | |
| DATED | : March 17, 2015 | |
| INVENTOR(S) | : James R. Wood | |

It is certified that error appears in the above-identified patent and that said Letters Patent is hereby corrected as shown below:

In the Claims

In claim 4, column 13, lines 37-38, replace:

"iteratively detecting, over a period of time, the modulated X-ray signal backscatter to generate a plurality images;" with --"iteratively detecting, over a period of time, the modulated X-ray signal backscatter to generate a plurality of images;"--.

In claim 8, column 13, lines 59-62, replace:

"The method of claim 1, further comprising processing the modulated X-ray signal backscatter to generate a three-dimensional image depicting the item, a location of the chemical element in the item." with --"The method of claim 1, further comprising processing the modulated X-ray signal backscatter to generate a three-dimensional image depicting the item and a location of the chemical element in the item."--.

Signed and Sealed this
First Day of December, 2015

Michelle K. Lee
*Director of the United States Patent and Trademark Office*